US010618857B2

(12) United States Patent
Di Girolamo et al.

(10) Patent No.: US 10,618,857 B2
(45) Date of Patent: Apr. 14, 2020

(54) PROCESS FOR THE SEPARATION OF $C_5$ HYDROCARBONS PRESENT IN STREAMS PREVALENTLY CONTAINING $C_4$ PRODUCTS USED FOR THE PRODUCTION OF HIGH-OCTANE HYDROCARBON COMPOUNDS BY THE SELECTIVE DIMERIZATION OF ISOBUTENE

(71) Applicant: SAIPEM S.p.A., San Donato Milanese (IT)

(72) Inventors: Marco Di Girolamo, San Donato Milanese-Milano (IT); Domenico Sanfilippo, Paullo-Milano (IT); Massimo Conte, Peschiera Borromeo-Milano (IT)

(73) Assignee: SAIPEM S.p.A., San Donato Milanese (IT)

( * ) Notice: Subject to any disclaimer, the term of this patent is extended or adjusted under 35 U.S.C. 154(b) by 0 days.

(21) Appl. No.: 14/589,465

(22) Filed: Jan. 5, 2015

(65) Prior Publication Data
US 2015/0225312 A1    Aug. 13, 2015

Related U.S. Application Data

(63) Continuation of application No. 12/094,061, filed as application No. PCT/EP2006/010893 on Nov. 13, 2006, now abandoned.

(30) Foreign Application Priority Data

Nov. 17, 2005   (IT) .............................. MI2005A2198

(51) Int. Cl.
*C07C 2/28*    (2006.01)
*C07C 7/06*    (2006.01)
(Continued)

(52) U.S. Cl.
CPC ................... *C07C 2/28* (2013.01); *C07C 7/06* (2013.01); *C07C 9/21* (2013.01); *C10G 50/00* (2013.01);
(Continued)

(58) Field of Classification Search
CPC .... C07C 7/06; C07C 9/21; C07C 2/28; C10G 50/00
See application file for complete search history.

(56) References Cited

U.S. PATENT DOCUMENTS 4,447,668 A    5/1984  Smith et al.
5,030,768 A    7/1991  Chen et al.
(Continued)

FOREIGN PATENT DOCUMENTS

EP    1 074 534      2/2001
WO    03/033442      4/2003

OTHER PUBLICATIONS

Fidkowski ("Distillation Configurations and Their Energy Requirements", AIChE Journal, Jun. 2006, vol. 52, No. 6).*

*Primary Examiner* — Brian A McCaig
*Assistant Examiner* — Jason Y Chong
(74) *Attorney, Agent, or Firm* — Oblon, McClelland, Maier & Neustadt, L.L.P.

(57) ABSTRACT

A process is described for the separation of $C_5$ hydrocarbons present, in a quantity ranging from 0.2 to 20% by weight, in streams prevalently containing $C_4$ products used for the production of high-octane hydrocarbon compounds, by the selective dimerization of isobutene, characterized in that the dimerization reaction is carried out in the presence of linear and branched alcohols and alkyl ethers in a quantity which is such as to have a molar ratio alcohols/alkyl ethers/isobutene in the feeding higher than 0.01.

19 Claims, 6 Drawing Sheets

(51) Int. Cl.
*C10G 50/00* (2006.01)
*C07C 9/21* (2006.01)

(52) U.S. Cl.
CPC ...... *C07C 2531/10* (2013.01); *C10G 2400/22* (2013.01)

(56) References Cited

U.S. PATENT DOCUMENTS

| | | |
|---|---|---|
| 5,908,964 A | 6/1999 | Koskinen et al. |
| 6,011,191 A | 1/2000 | Di Girolamo et al. |
| 6,433,238 B1 | 8/2002 | Di Girolamo et al. |
| 6,590,132 B1 | 7/2003 | Vora |
| 6,613,108 B1 | 9/2003 | Aittamaa et al. |
| 6,734,333 B2 | 5/2004 | Loescher |
| 2006/0122444 A1 | 6/2006 | Peters et al. |

\* cited by examiner

PROCESS FOR THE SEPARATION OF C$_5$ HYDROCARBONS PRESENT IN STREAMS PREVALENTLY CONTAINING C$_4$ PRODUCTS USED FOR THE PRODUCTION OF HIGH-OCTANE HYDROCARBON COMPOUNDS BY THE SELECTIVE DIMERIZATION OF ISOBUTENE

CROSS REFERENCE TO RELATED APPLICATIONS

The present application is a continuation application of Ser. No. 12/094,061 having a filing date of Aug. 15, 20018, now abandoned, which is a national stage application of PCT/EP06/10894 having a filing date of Nov. 13, 2006 and claims priority to Italian patent application MI2005A002198 having a filing date of Nov. 17, 2005.

The present invention relates to a process for the separation of C$_5$ hydrocarbons present in the C$_4$ charges used for the production of high-octane hydrocarbon compounds by the selective dimerization reaction of isobutene and to a lesser extent of possible linear olefins, in the presence of linear and branched alcohols and alkyl ethers, which favour the production of higher selectivities on the part of the catalyst. The mixture obtained can then be hydrogenated with conventional methods to obtain a product with further enhanced octane characteristics.

For mainly environmental reasons, the composition of gasolines is being reformulated and the general tendency is towards the production of fuels which burn better and have lower evaporative emissions. The main measures for achieving this objective are listed below (D. Sanfilippo, F. Ancillotti, M. Marchionna, Chim. & Ind., 76, (1994), 32):
  reduction in the content of aromatic compounds and elimination of benzene;
  reduction in the volatility of gasolines to minimize evaporative losses;
  reduction in the content of light olefins, photochemically extremely reactive;
  reduction in the sulfur content and final boiling point of the gasolines.

All these measures consequently create the necessity of projecting new production processes of purely hydrocarbon compounds capable of positively contributing to the above demands.

Among these, alkylated products are extremely important as they have a high octane number, a low volatility and are practically free of olefins and aromatic compounds. The alkylation process in liquid phase is a reaction between isoparaffinic hydrocarbons, such as isobutane, and olefins, for example propylene, butenes, pentenes and relative mixtures thereof, in the presence of an acid catalyst for the production of C$_7$-C$_9$ hydrocarbons with a high octane number to be used in gasolines (A. Corma, A. Martinez, Catal. Rev.—Sci. Eng., 35, (1993), 483).

The main problem of alkylation processes is due to the fact that, with growing environmental regulations, both of the traditional processes (with hydrofluoric and sulfuric acid) are encountering considerable difficulties, which create uncertainties for the future; the process with hydrofluoric acid due to the toxicity of this acid, especially in populated areas, and that using sulfuric acid, as a result of the large production of acid sludge as well as the considerably corrosive nature of the catalyst.

Alternative processes with solid acid catalysts are being developed but their commercial applicability has yet to be demonstrated.

A hydrocarbon product of this type, on the other hand, is becoming increasingly more requested due to its octane characteristics (both the Research Octane Number (RON) and the Motor Octane Number (MON) are high) and those relating to the boiling point (limited volatility but low end-point) which position it in the group of compositions of great interest for obtaining gasolines which are more compatible with current environmental requirements.

An alternative refinery process for obtaining products with characteristics similar to those of alkylated products can be offered by the hydrogenation of so-called "polymer" gasoline.

Oligomerization processes (often inaccurately called polymerization in the refining industry) were widely used in the '30s' and '40s' for converting low-boiling C$_3$-C$_4$ olefins into gasolines. The process leads to the production of a gasoline with a high octane number (RON about 97) but with a high sensitivity (difference between RON and MON) due to the purely olefinic nature of the product (J. H. Gary, G. E. Handwerk, "Petroleum Refining: Technology and Economics", 3$^{rd}$ Ed., M. Dekker, New York, (1994), 250).

Typical olefins which are oligomerized are mainly propylene, which gives dimers or slightly higher oligomers depending on the process used, and isobutene which mainly gives dimers but is always accompanied by a considerable quantity of higher oligomers.

With particular attention to the oligomerization of isobutene, it is known that this reaction can be carried out either batchwise, semi-batchwise or in continuous, either in gas or liquid phase, generally at temperatures ranging from 50 to 300° C. and at atmospheric pressure or such pressures as to maintain the reagents in liquid phase, if necessary.

Typical catalysts for the industrial oligomerization process of isobutene are represented by phosphoric acid, generally supported on a solid (for example kieselguhr), or cation-exchange acid resins. The latter allow blander conditions to be used compared with supported phosphoric acid both in terms of temperature and pressure (50-100° C. and 0.2-3 MPa with respect to 200-220° C. and 3-10 MPa).

Other catalysts are also claimed in literature, both liquid acids such as H$_2$SO$_4$ and derivatives of sulfonic acids, and solids such as silico-aluminas, mixed oxides, zeolites, fluorinated or chlorinated aluminas, etc.; none of these catalysts however has so far enabled an industrial process to be set up, as in the case of supported phosphoric acid (F. Asinger, "Mono-olefins: Chemistry and Technology", Pergamon Press, Oxford, pages 435-456) and that of cation resins (G. Scharfe, Hydrocarbon Proc., April 1973, 171).

From the product point of view, the main problem of this process lies in the fact that excessive percentages of heavy oligomers such as trimers (selectivity of 20-40%) and tetramers (selectivity of 1-5%) of isobutene, are produced in the oligomerization phase. Tetramers are completely outside the gasoline fraction as they are too high-boiling and therefore represent a net loss in yield to gasoline; as far as trimers are concerned, their concentration should be greatly reduced as they have a boiling point (170-180° C.) at the limit of future specifications on the final point of reformulated gasolines.

The problem of reducing the formation of oligomers higher than dimers to percentages lower than 15% is, on the other hand, a problem typical of the oligomerization of isobutene, as also indicated in literature (C. T. O'Connor, M. Kojima, K. W. Shcumann, Appl. Catal., 16, (1985), 193). This level of heavy compounds is slightly higher than that of an alkylated product and is still tolerated in the gasoline pool.

From what is specified above, there is evidently great interest in obtaining a new dimerization process of isobutene which allows the synthesis of a higher-quality product, through reaching greater selectivities.

BRIEF SUMMARY OF THE INVENTION

One aspect of the invention is a process for separating $C_5$ hydrocarbons from a hydrocarbon stream prevalently containing $C_4$ products and for use in high-octane hydrocarbon compounds.

In another aspect of the invention the $C_5$ hydrocarbons are separated by the selective dimerization of isobutene in the presence of alcohols.

In another aspect of the invention the separation is effected using traditional fractionation columns.

By carrying out the selective dimerization reaction of isobutene in the presence of moderate quantities of linear and branched alcohols and alkyl ethers, the production of a fraction of oligomers is selectively obtained, which is particular rich in dimers (>85%) and practically free of tetramers and higher oligomers (<0.5%).

The reaction product is then preferably hydrogenated to give a completely saturated end-product with a high octane number and low sensitivity.

The hydrogenation can be carried out with conventional methods as described, for example, in F. Asinger, "Monoolefins: Chemistry and Technology", Pergamon Press, Oxford, page 455.

For illustrative purposes, Table 1 indicates the octane number and relative boiling points of some of the products obtained, by means of the process, object of the present invention.

TABLE 1

| Product | RON | MON | b.p. (° C.) |
|---|---|---|---|
| Diisobutenes | 100 | 89 | 100-105 |
| Iso-octane | 100 | 100 | 99 |
| Tri-isobutenes | 100 | 89 | 175-185 |
| Hydrogenated tri-isobutenes | 101 | 102 | 170-180 |

The process, object of the present invention, for the separation of $C_5$ hydrocarbons present, in a quantity ranging from 0.2 to 20% by weight, in streams prevalently containing $C_4$ products used for the production of high-octane hydrocarbons, by the selective dimerization reaction of isobutene, is characterized in that the reaction is carried out in the presence of linear and branched alcohols and ethers in a quantity which is such as to have a molar ratio alcohols+ethers/isobutene in the feeding higher than 0.01 and preferably lower than 0.7.

It should also be pointed out that in the case of hydrocarbon streams also comprising $C_4$ and $C_5$ olefins, it has been observed that at least a part of the latter can be converted by reaction with isobutene into the hydrocarbon product without altering the octane value. It is therefore preferable to effect an enriching treatment, by means of pre-isomerization, of the internal linear olefins, in order to favour the overall octane number of the mixture.

The process claimed herein can be applied to cuts mainly containing isobutane, isobutene, n-butane, n-butenes and saturated and olefinic $C_5$ hydrocarbons.

Although a wide variety of sources are available for the supply of these streams, the most common are those deriving from Dehydrogenation processes of iso-paraffins, from FCC units, Steam Cracking or processes for the production of pure isobutene such as the dehydration of tertbutyl alcohol (TBA) or the Cracking of MTBE and/or ETBE; these streams differ from each other in the content of isobutene and linear butenes, as shown in Table 2.

TABLE 2

| | Steam Cracking | FCC | Dehydrogenation | Pure isobutene |
|---|---|---|---|---|
| Isobutene | 30-50 | 10-25 | 45-55 | >90 |
| n-butenes | 35-60 | 25-50 | 1-2 | <10 |
| Saturated $C_4$ | 4-10 | 30-60 | 45-55 | <1 |

Should streams from Steam Cracking contain diolefins in addition to the desired mono-olefins, they must be eliminated by means of typical removal treatment (for example solvent extraction or selective hydrogenation).

Saturated and olefinic $C_5$ hydrocarbons can be present in these streams, in various amounts (0.2-20% by weight), depending on the efficiency of the $C_4$-$C_5$ separation step. The $C_5$ olefins possibly present can be involved in dimerization reactions.

The stream sent to the reaction steps can contain branched alcohols or a blend of alcohols and alkyl ethers, in addition to the hydrocarbon components.

The alcohols used are linear, preferably containing a number of carbon atoms ranging from 1 to 6, preferably from 4 to 7 carbon atoms; preferred linear alcohols are methanol and/or ethanol, whereas preferred branched alcohols are tert-butyl alcohol (TBA) and/or tert-amyl alcohol (TAA).

The alkyl ether used can be selected from those containing a number of carbon atoms ranging from 5 to 10: MTBE (methyl tert-butyl ether), ETBE (ethyl tert-butyl ether), MSBE (methyl sec-butyl ether), ESBE (ethyl sec-butyl ether), TAME (methyl tert-amyl ether), TAEE (ethyl tertamyl ether) or mixtures thereof are preferred.

Isobutene, together with the hydrocarbon stream in which it is contained, is sent with the mixture of alcohols and alkyl ethers, in stoichiometric defect, into contact with the acid catalyst where the dimerization takes place.

The linear primary alcohol, in addition to interacting with the catalyst, also helps to limit the possible cracking of the alkyl ether and can possibly react with the dimers and linear $C_4$ olefins, whereas the branched alcohol (tertiary) does not react with the olefins due to its steric hindrance.

In order to obtain the dimerization product with the desired selectivity to dimers, it is essential to maintain a constant level of oxygenated products in the reaction environment but above all the contemporaneous presence of the three oxygenated compounds (linear alcohol, branched alcohol and alkyl ether) which, due to a synergic effect are capable of forming the catalytic species with the correct activity and stability. The optimal level of the sum of alcohols and alkyl ethers which should be present in the reaction environment to obtain selectivities to dimers close to 85% by weight, depends on the composition of the hydrocarbon charge. The higher the olefin content in the charge, the lower the amount of oxygenated products to be used.

A wide variety of acid catalysts can be used for this process, but those preferred are styrene-divinyl benzene polymeric resins having sulphonic groups as catalytic centres.

A large range of operative conditions can be used to produce high-octane hydrocarbons from isobutene in the desired selectivities. It is possible to operate in vapour or liquid-vapour phase, but operating conditions in liquid phase are preferred.

The pressure is preferably higher than the atmospheric value, in order to maintain the reagents in liquid phase, generally below 5 MPa, more preferably between 0.2-2.5 MPa. The reaction temperature preferably ranges from 30 to 120° C.

The feeding space velocities of the oxygenated-hydrocarbon stream are preferably lower than 30 $h^{-1}$, more preferably ranging from 1 and 15 $h^{-1}$.

Isobutene is mainly converted in the reaction zone, however part of the $C_4$-$C_5$ olefins present can also be converted to useful product; in principle, there are no limits to the concentration of iso-olefin in the hydrocarbon fraction, even if concentrations ranging from 2 to 60% are preferred; in case of streams having a high isobutene concentration (dehydration or cracking) it is therefore convenient to dilute the charge with $C_4$-$C_7$ hydrocarbons. There are no limits, on the contrary, for the ratio between isobutene and linear olefins.

The process, object of the present invention, can be effected batchwise or in continuous, bearing in mind however that the latter is much more advantageous in industrial practice. The reactor configuration selected is generally a double reaction step comprising one or more fixed bed reactors which can be optionally selected from a tubular and adiabatic reactor.

The presence of $C_5$ hydrocarbons in the feed, however, complicates the process schemes, as these compounds have intermediate boiling temperatures between $C_4$ and oxygenated products, and they also form azeotropic mixtures with the branched alcohols as shown in Table 3, which indicates the boiling points of the most representative low-boiling components present in the streams

TABLE 3

| Compound | Boiling point, ° C. |
| --- | --- |
| $C_4$/Methanol azeotropic product | −5 |
| $C_4$ products | −12/1 |
| Isopentane/TBA azeotropic product | 25 |
| Isopentane | 28 |
| 1-pentene | 30 |
| 2-methyl-1-butene | 31 |
| n-pentane | 36 |
| 2-methyl-2-butene | 39 |
| Cyclopentane | 49 |
| MTBE | 55 |
| Methanol | 65 |
| Dimers/TBA azeotropic product | 78 |

TABLE 3-continued

| Compound | Boiling point, ° C. |
| --- | --- |
| TBA | 82 |
| Dimers | 100-105 |

The $C_5$ products cannot therefore be removed from the plant together with the $C_4$ products, as they would introduce oxygenated products (branched alcohols and ethers) into the stream, which are difficult to remove by means of the traditional techniques used for removing methanol (water washing) and which are poisonous for the subsequent treatment processes of the streams (polymerization, alkylation and metathesis). The $C_5$ products, on the other hand, cannot be maintained in the oxygenated stream as they would rapidly accumulate. With respect to the schemes shown in literature (U.S. Pat. No. 6,011,191), it is therefore necessary to introduce a $C_5$/branched alcohol azeotropic separation step, which can be inserted in different positions of the plant in relation to the $C_5$ content in the charge and also the relative concentration of the $C_5$ products present.

The separation of the $C_5$/branched alcohol azeotropic product can be effected using traditional fractionation columns in which the azeotropic mixture can be recovered at the head, bottom or as side cut.

The process, object of the present invention, can be carried out, in particular, by means of the following essential steps:

a) feeding a stream containing isobutene and $C_5$ hydrocarbons, together with one or more streams containing oxygenated products (linear and branched alcohols, ethers and water), to one or more reaction steps (consisting of one or more reactors);

b) separating the $C_4$/linear alcohol azeotropic product and possibly the $C_4$ products from the $C_5$ hydrocarbons, from the remaining oxygenated products and from the hydrocarbon product, in one or more distillation columns;

c) recovering the linear alcohol from the azeotropic mixture with the $C_4$ products by means of conventional processes such as washing with water or absorption on inorganic solids;

d) separating the $C_5$ products (as an azeotropic compound with the branched alcohol) from the remaining oxygenated products and from the reaction product, in one or more distillation columns, in order to obtain three streams with the desired purity;

e) recycling the stream containing the remaining oxygenated products and that containing the linear alcohol recovered, to the two reaction steps;

f) feeding linear alcohol and water (which forms the branched alcohol in the reactors by reaction with the tertiary olefin) to the reaction steps to compensate the losses of linear alcohol, which can react with the dimers and linear $C_4$ olefins, and branched alcohol which, on the contrary, leaves the plant together with the $C_5$ products;

g) recycling part of the $C_4$ products, with or without linear alcohol, to the reaction steps in order to maximize the isobutene conversion.

For the process comprising the essential steps indicated above, the $C_5$ products are present in the streams prevalently containing $C_4$ products in a quantity preferably ranging from 0.5 to 10% by weight.

The separation of the $C_5$/branched alcohol azeotropic product is preferably carried out starting from blends of:

a) $C_5$—oxygenated products (ethers and branched alcohols)—reaction product, wherein the $C_5$ hydrocarbons are recovered as an azeotropic compound with the branched alcohol as head effluent using a scheme based on a column, with recovery of the remaining oxygenated products as side cut, or two fractionation columns;

b) $C_5$—oxygenated products (ethers and branched alcohols)—dimers, wherein the $C_5$ hydrocarbons are recovered as an azeotropic compound with the branched alcohol as head effluent of a fractionation column;

c) $C_4$-$C_5$—oxygenated products (ethers and branched alcohols)—reaction product, effluent from a reaction step, wherein the $C_5$ hydrocarbons are recovered as an azeotropic compound with the branched alcohol as side cut of a fractionation column from whose head the $C_4$/linear alcohol azeotropic product and possibly the $C_4$ products are recovered, whereas a mixture containing the oxygenated products and the reaction product is recovered at the bottom;

d) $C_4$-$C_5$—oxygenated products (linear and branched alcohols) wherein the $C_5$ hydrocarbons are recovered as an azeotropic compound with the branched alcohol as bottom effluent of a fractionation column from whose head the $C_4$/linear alcohol azeotropic product and possibly the $C_4$ products are recovered.

Six process schemes are shown in FIGS. 1-6, in order to clearly illustrate the present invention.

Figure 1:
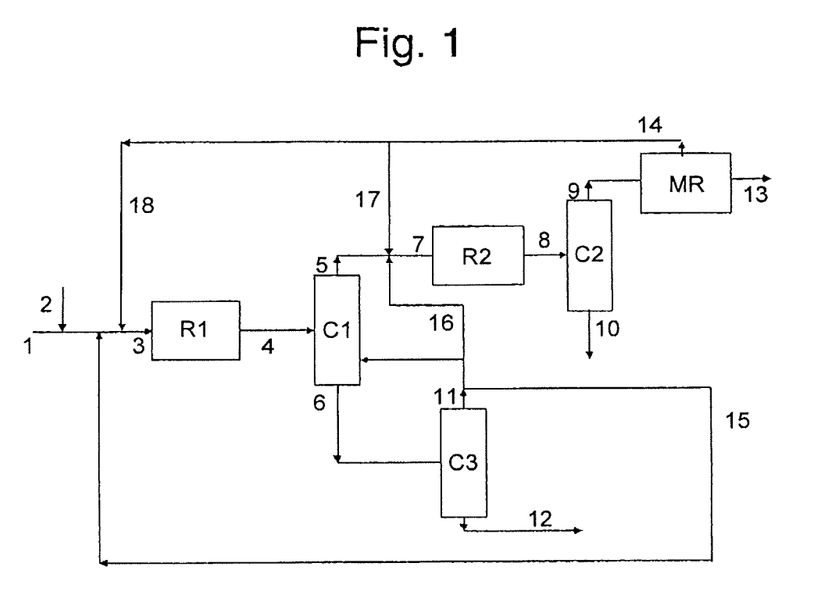
FIG. 1 shows a process scheme according to the invention where $C_5$ hydrocarbons are not present in the feed delay reaction.

FIG. 1 shows a process scheme wherein $C_5$ hydrocarbons are not present in the charge and the oxygenated products are methanol (linear alcohol), TBA (branched alcohol) and MTBE (alkyl ether).

The stream (1) containing isobutene, together with the reintegration feeding of methanol and water (2) and the recycled streams of oxygenated products (MTBE and TBA) (15) and methanol (18), is sent to a first reaction step R1, which can consist of one or more reactors, in which the $C_4$ iso-olefin is selectively converted to dimers.

The effluent (4) from the first reaction step, is sent to a first separation column C1 in which a stream (5) essentially containing $C_4$ hydrocarbons and methanol is removed from the head, whereas a stream (6) essentially containing the reaction product and remaining oxygenated compounds, is collected at the bottom.

The head stream (5) is then fed, together with the recycled streams of oxygenated products (16) and methanol (17), to a second reaction step R2, which can consist of one or more reactors, wherein the isobutene present is selectively converted to dimers.

The effluent (8) from the second reaction step is separated in a column C2 from whose bottom a stream (10) essentially containing MTBE, TBA, the dimerization product and part of the $C_4$ products, is removed and sent to the column C1 for the recovery of the product and oxygenated products. The head stream (9), consisting of $C_4$ products and the $C_4$/methanol azeotropic mixture is, on the other hand, sent to an MR unit for the recovery of the alcohol which can consist, for example, of an absorption system on molecular sieves or a water washing column. In both cases, the alcohol recovered (14) can be sent back to the two reaction steps (streams 17 and 18) whereas the hydrocarbon stream (13) can be used in subsequent operations.

The bottom stream (6) of the column C1 is sent to a further separation column C3 wherein a stream (11) essentially containing MTBE, TBA and dimers is removed at the head and is recycled to the two reaction steps (streams 15 and 16), whereas the reaction product (12) essentially consisting of dimers, trimers and small quantities of oligomers and ethers of dimers, is recovered at the bottom.

When $C_5$ hydrocarbons are present in the charge, on the contrary, according to the present invention, different plant configurations can be used, schematised in the following FIGS. 2-6, to recover the $C_5$/TBA azeotropic product, depending on the quantity of $C_5$ products present and the required purity of the streams.

Figure 2:
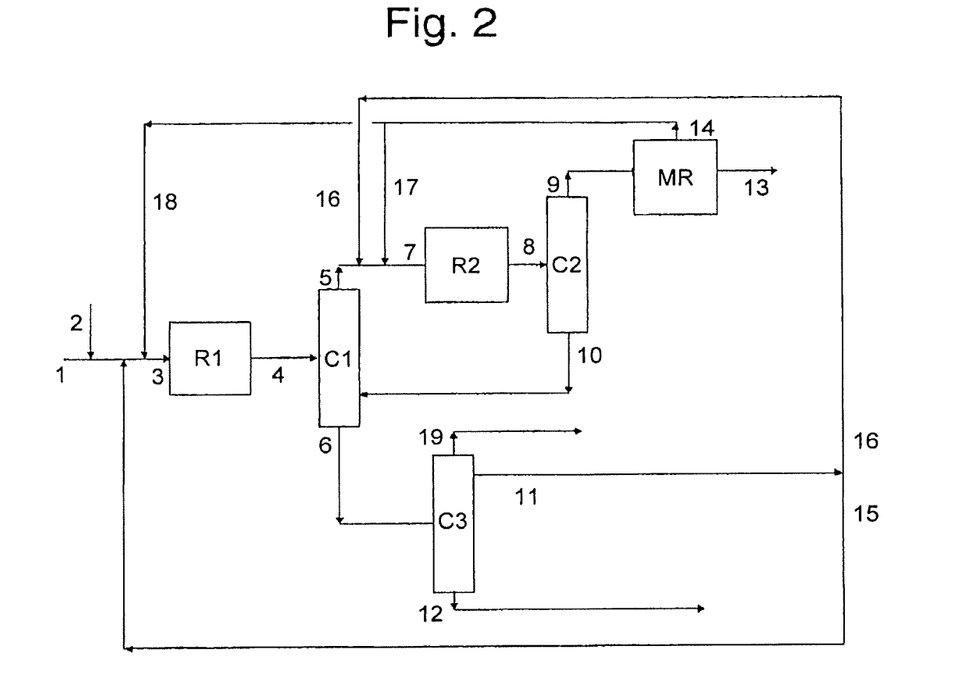
FIG. 2 shows a process scheme according to the invention in which oxygenated products are recycled.

FIG. 2 therefore shows a possible process scheme which differs from the previous scheme in that the stream containing oxygenated products to be recycled (11) (ethers and TBA) is removed from the column C3 as side cut, whereas the $C_5$/TBA azeotropic product (19) is recovered from the head of the column and can optionally be joined with the reaction product.

Figure 3:
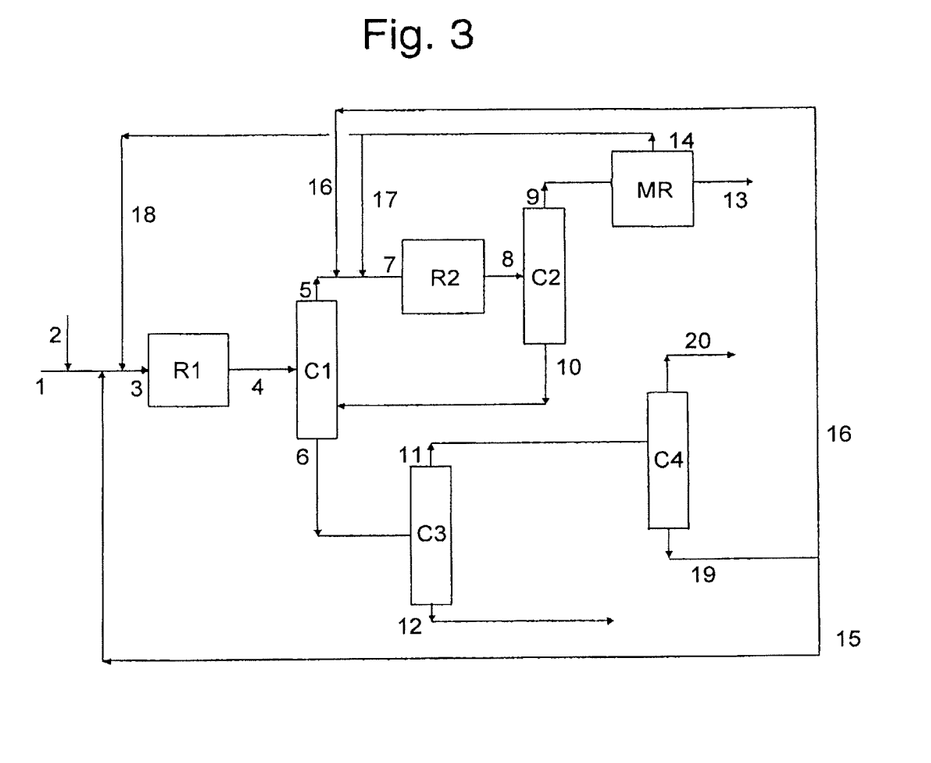
FIG. 3 shows a process scheme of the invention in which a head stream is sent to a column.
Figure 4:
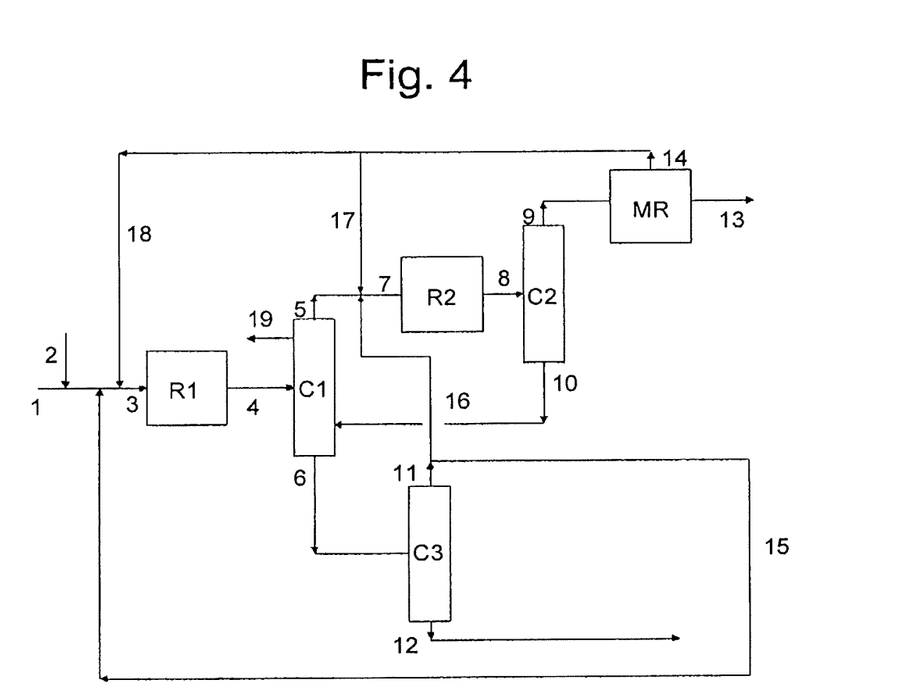
FIG. 4 shows a process scheme of the reaction in which an azeotropic mixture is recovered.

The process scheme becomes more complex when a more efficient separation of the mixture of $C_5$ products/oxygenated products/reaction product is to be effected, as a new fractionation column C4 must be inserted, as shown in FIG. 3. In this new scheme, the head stream of the column C3 (11) is sent to a new column C4 where the $C_5$/TBA azeotropic mixture (20) is separated at the head and the stream of oxygenated products (19) is separated at the bottom and recycled to the two reaction steps.

Figure 5:
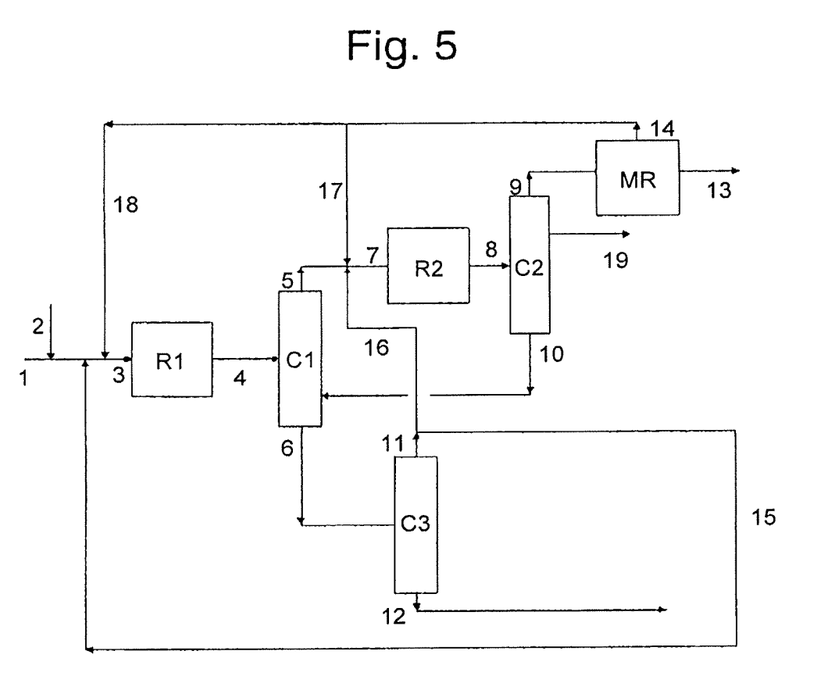
FIG. 5 shows a process scheme of the invention in which an azeotropic mixture is recovered in a column.
Figure 6:
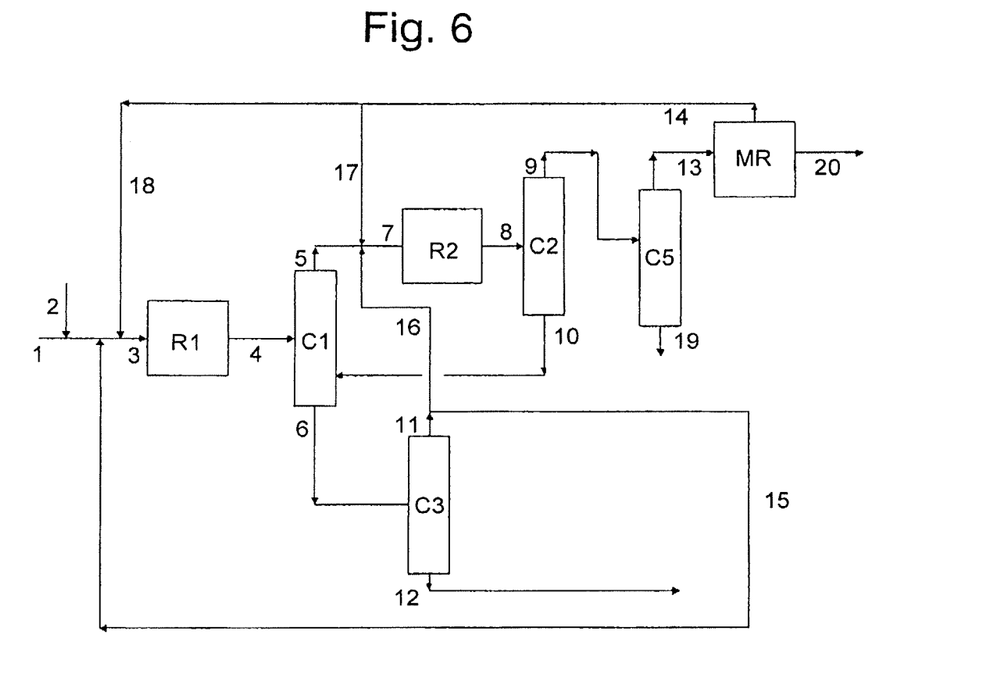
FIG. 6 shows a reaction scheme according to the invention which products are separated in a column.

Alternatively, the $C_5$ hydrocarbons can be recovered using the two fractionation columns of the $C_4$ products wherein the $C_5$/TBA azeotropic mixture can be thus recovered as side cut (19) both in the column C1 (FIG. 4) and in the column C2 (FIG. 5). A further option however consists in effecting the separation of the $C_4$-$C_5$ products in a last new column C5, as shown in FIG. 6, in which the $C_5$/TBA azeotropic product is recovered as bottom stream (19).

The invention claimed is:

1. A process for the separation of $C_5$ hydrocarbons present, in a quantity ranging from 0.2 to 20% by weight, in at least one hydrocarbon stream prevalently containing O4 products for the production of high-octane hydrocarbon compounds, comprising:

selectively dimerizing isobutene in one or more reaction steps in the presence of an oxygenated hydrocarbon stream comprising at least one linear alcohol, at least one tertiary branched alcohol and at least one alkyl ether, wherein the branched alcohol forms a $C_5$/branched alcohol azeotrope mixture with the Cs hydrocarbons, wherein the oxygenated hydrocarbon stream is present in such a quantity as to have a molar ratio of (alcohols+alkyl ethers)/isobutene of greater than 0.01, and separating the $C_5$/branched alcohol azeotrope mixture and an oxygenated stream comprising the at least one tertiary branched alcohol and the at least one alkyl ether from a dimerization product comprising dimers, and recycling the oxygenated stream to the one or more reaction steps, wherein the separating of the $C_5$/branched alcohol azeotrope mixture and the oxygenated stream is carried out by one of the following steps:

subjecting a dimerization effluent from the one or more reaction steps to a distillation column to produce a top stream comprising undimerized isobutene and the at least one linear alcohol and a bottom stream comprising the $C_5$/branched alcohol azeotrope mixture, the at least one tertiary branched alcohol, the at least one alkyl ether, and the dimerization product, and then subjecting the bottom stream to one or more fractionation columns to produce (i) a stream comprising the $C_5$/branched alcohol azeotrope mixture, (ii) the oxygenated stream comprising the at least one tertiary branched alcohol and the at least one alkyl ether, and (iii) a product stream comprising the dimerization product;

subjecting a dimerization effluent from the one or more reaction steps to a distillation column to produce a top stream comprising undimerized isobutene and the at least one linear alcohol, a side stream comprising the $C_5$/branched alcohol azeotrope mixture, and a bottom stream comprising the at least one tertiary branched alcohol, the at least one alkyl ether, and the dimerization product, and then subjecting the bottom cut to another fractionation column to obtain (i) the oxygenated stream comprising the at least one tertiary branched alcohol and the at least one alkyl ether and (ii) a product stream comprising the dimerization product; or subjecting a dimerization effluent from the one or more reaction steps to a distillation column to produce a top stream comprising undimerized isobutene and the at least one linear alcohol and the $C_5$/branched alcohol azeotrope mixture and a bottom stream comprising the at least one tertiary branched alcohol, the at least one alkyl ether, and the dimerization product, subjecting the top steam to one or more separation columns to produce a stream comprising the $C_5$/branched alcohol azeotrope mixture, and subjecting the bottom stream to another fractionation column to obtain to obtain (i) the oxygenated stream comprising the at least one tertiary branched alcohol and the at least one alkyl ether and (ii) a product stream comprising the dimerization product.

2. The process according to claim 1, wherein the molar ratio (alcohols+alkyl ethers)/isohutene is lower than 0.7.

3. The process according to claim 1, wherein the dimerizing is carried out at a temperature of from 30 to 120° C., at a pressure lower than 5 MPa and at a feeding space velocity lower than 30 h$^{-1}$.

4. The process according to claim 1 wherein the dimerizing is carried out at a feeding space velocity of from 1 to 15 h$^{-1}$.

5. The process according to claim 1, wherein the linear-alcohol has a number of carbon atoms of from 1 to 6.

6. The process according to claim 5, wherein the linear alcohol is at least one of methanol and/or ethanol.

7. The process according to claim 1, wherein the branched alcohol has a number of carbon atoms of from 4 to 7.

8. The process according to claim 7, wherein the branched alcohol is at least one of tert-butyl alcohol and/or tert-amyl alcohol.

9. The process according to claim 1, wherein the alkyl ether has a number of carbon atoms of from 5 to 10.

10. The process according to claim 9, wherein the alkyl ether is at least one selected from the group consisting of MTBE, ETBE, MSBE, ESBE, TAME, TAEE and mixtures thereof.

11. The process according to claim 1, wherein the hydrocarbon stream further comprises one or more other olefins to form high octane products.

12. The process according to claim 1, wherein the isobutene content in the hydrocarbon stream is modified by dilution with $C_4$-$C_7$ streams.

13. The process according claim 1, further comprising the following steps:

a) feeding a $C_4$-$C_5$ hydrocarbon cut containing isobutene, together with one or more streams containing one or more of a linear alcohol, a tertiary branched alcohol, an ether and water, to one or more reaction steps, comprising one or more reactors;

b) separating a $C_4$/linear alcohol azeotropic product and optionally one or more $C_4$ products from the $C_5$ hydrocarbons, from a remaining oxygenated product and from a hydrocarbon product, in one or more distillation columns;

c) recovering the linear alcohol from the $C_4$/'linear alcohol azeotropic product by at least one of washing with water and absorption on inorganic solids;

d) separating the $C_5$/branched alcohol azeotrope mixture from remaining oxygenated products and from the dimerization product, in one or more fractionation column, in order to obtain a $C_5$/branched alcohol azeotrope mixture stream, an oxygenated stream comprising the tertiary branched alcohol and the ether, and a reaction product stream comprising dimers and/or oligomers with a desired purity;

e) recycling the recovered linear alcohol to the one or more reaction steps;

f) feeding a linear alcohol and water, which forms the branched alcohol in the reactors by reaction with a tertiary olefin, to the reaction steps to compensate losses of the linear alcohol, which can react with dimers and linear $C_4$ olefins, and the branched alcohol which leaves together with the $C_5$ products;

g) recycling part of the $C_4$ hydrocarbon products, with or without the linear alcohol, to the reaction steps in order to maximize an isobutene conversion.

14. The process according to claim 13, wherein the $C_5$ hydrocarbons are present in the hydrocarbon stream in a quantity of from 0.5 to 10% by weight.

15. The process according to claim 1, further comprising:

joining the $C_5$/branched alcohol azeotrope mixture with the dimerization product.

16. The process according to claim 1, wherein the dimerizing is carried out in one or more of a fixed bed reactor, a tubular reactor and an adiabatic reactor.

17. The process according to claim 1, wherein the $C_5$/branched alcohol azeotrope mixture comprises a saturated $C_5$ hydrocarbon.

18. The process according to claim 1, wherein the separating removes the $C_5$ hydrocarbon from the oxygenated hydrocarbon stream after the dimerizing to form a dimerization product depleted in $C_5$ hydrocarbons.

19. A process for continuously separating $C_5$ hydrocarbons from a hydrocarbon stream comprising 0.5 to 20% by weight $C_5$ hydrocarbons and a majority of $C_4$ products, comprising:

selectively dimerizing isobutene in one or more reaction steps in the presence of an oxygenated hydrocarbon stream comprising at least one linear alcohol, at least one tertiary branched alcohol and at least one alkyl ether, wherein the branched alcohol forms a $C_5$/branched alcohol azeotrope mixture with the Cs hydrocarbons, wherein the oxygenated hydrocarbon stream is present in such a quantity as to have a molar ratio of (alcohols+alkyl ethers)/isobutene of greater than 0.01, and separating the $C_5$/branched alcohol azeotrope mixture and an oxygenated stream comprising the at least one tertiary branched alcohol and the at least one alkyl ether from a dimerization product, and recycling the oxygenated stream to the one or more reaction steps, wherein the level of the linear alcohol, the tertiary branched alcohol and the alkyl ether remains constant during the selectively dimerizing isobutene, wherein the linear alcohol is methanol, the branched alcohol is TBA, and the alkyl ether is MTBE, and wherein the separating of the $C_5$/branched alcohol azeotrope mixture and the oxygenated stream is carried out by one of the following steps:

subjecting a dimerization effluent from the one or more reaction steps to a distillation column to produce a top stream comprising undimerized isobutene and the at least one linear alcohol and a bottom stream comprising the $C_5$/branched alcohol azeotrope mixture, the at least one tertiary branched alcohol, the at least one alkyl ether, and the dimerization product, and then subjecting the bottom stream to one or more fractionation columns to produce (i) a stream comprising the $C_5$/branched alcohol azeotrope mixture, (ii) the oxygenated stream comprising the at least one tertiary branched alcohol and the at least one alkyl ether, and (iii) a product stream comprising the dimerization product;

subjecting a dimerization effluent from the one or more reaction steps to a distillation column to produce a top stream comprising undimerized isobutene and the at least one linear alcohol, a side stream comprising the $C_5$/branched alcohol azeotrope mixture, and a bottom stream comprising the at least one tertiary branched alcohol, the at least one alkyl ether, and the dimerization product, and then subjecting the bottom cut to another fractionation column to obtain (i) the oxygenated stream comprising the at least one tertiary branched alcohol and the at least one alkyl ether and (ii) a product stream comprising the dimerization product; or subjecting a dimerization effluent from the one or more reaction steps to a distillation column to produce a top stream comprising undimerized isobutene and the at least one linear alcohol and the $C_5$/branched alcohol azeotrope mixture and a bottom stream comprising the at least one tertiary branched alcohol, the at least one alkyl ether, and the dimerization product, subjecting the top steam to one or more separation columns to produce a stream comprising the $C_5$/branched alcohol azeotrope mixture, and subjecting the bottom stream to another fractionation column to obtain to obtain (i) the oxygenated stream comprising the at least one tertiary branched alcohol and the at least one alkyl ether and (ii) a product stream comprising the dimerization product.

* * * * *